(12) United States Patent
Romoscanu

(10) Patent No.: US 10,010,700 B2
(45) Date of Patent: Jul. 3, 2018

(54) CONTROL HANDLES FOR CATHETERS

(71) Applicant: ST. JUDE MEDICAL LUXEMBOURG HOLDING S.À.R.L., Luxembourg (LU)

(72) Inventor: Alexandre Ioan Romoscanu, Geneva (CH)

(73) Assignee: ST JUDE MEDICAL INTERNATIONAL HOLDING S.À F, Luxembourg (LU)

( * ) Notice: Subject to any disclaimer, the term of this patent is extended or adjusted under 35 U.S.C. 154(b) by 212 days.

(21) Appl. No.: 14/799,745

(22) Filed: Jul. 15, 2015

(65) Prior Publication Data

US 2016/0030715 A1    Feb. 4, 2016

Related U.S. Application Data

(63) Continuation of application No. 13/930,988, filed on Jun. 28, 2013, now Pat. No. 9,095,682.

(60) Provisional application No. 61/819,335, filed on May 3, 2013, provisional application No. 61/817,661, filed on Apr. 30, 2013.

(51) Int. Cl.
*A61M 31/00* (2006.01)
*A61M 37/00* (2006.01)
*A61M 25/01* (2006.01)

(52) U.S. Cl.
CPC .... *A61M 25/0147* (2013.01); *A61M 25/0133* (2013.01); *A61M 25/0136* (2013.01)

(58) Field of Classification Search
CPC .......... A61M 25/0133; A61M 25/0136; A61M 25/0147
See application file for complete search history.

(56) References Cited

U.S. PATENT DOCUMENTS 4,203,430 A    5/1980    Takahashi
5,364,351 A    11/1994   Heinzelman
(Continued)

FOREIGN PATENT DOCUMENTS

CN    101626723 A    1/2010
DE    10034105 C1    4/2002
(Continued)

OTHER PUBLICATIONS

International Search Report for PCT Application No. PCT/IB2014/001664, dated Mar. 10, 2015, 16 pages.

*Primary Examiner* — Rebecca E Eisenberg
(74) *Attorney, Agent, or Firm* — Dykema Gossett PLLC

(57) ABSTRACT

A plunger-type control handle for controlling the deflection of a distal tip of a catheter. The control handle includes a spool driven by a gear, the spool being connected to the proximal end of at least one pull wire. For bi-directional deflection, a second proximal end of a pull wire is connected to the spool such that when one of the proximal ends is collected by the spool, the other of the proximal ends is released in an equal amount. The gear is operatively coupled to the plunger and engages a gear rack disposed on the control handle housing, such that when there is relative movement between the housing and the plunger, the gear and spool are rotated. In one embodiment, a switching mechanism is provided that reverses the rotation direction of the gear and spool, thereby providing full stroke resolution of the plunger in each of the bi-directional directions.

16 Claims, 9 Drawing Sheets

(56) References Cited

U.S. PATENT DOCUMENTS

| | | | |
|---|---|---|---|
| 5,383,852 A | 1/1995 | Stevens-Wright | |
| 6,198,974 B1 | 3/2001 | Webster, Jr. | |
| 6,210,407 B1 | 4/2001 | Webster | |
| 2005/0277874 A1* | 12/2005 | Selkee | A61M 25/0136 604/95.04 |
| 2007/0078455 A1 | 4/2007 | Rashidi | |
| 2010/0069834 A1* | 3/2010 | Schultz | A61M 25/0136 604/95.04 |
| 2011/0251554 A1 | 10/2011 | Romoscanu | |

FOREIGN PATENT DOCUMENTS

| | | |
|---|---|---|
| JP | 59031202 Y | 9/1984 |
| JP | H06-292728 A | 10/1994 |
| WO | 2012019232 | 2/2012 |

\* cited by examiner

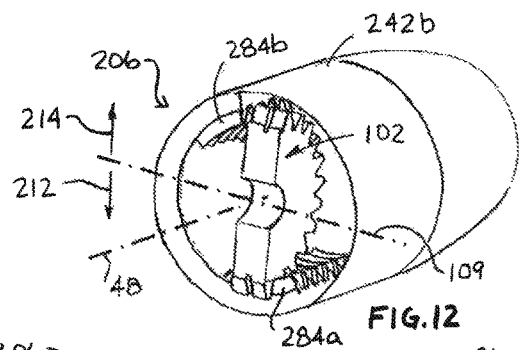
FIG. 12
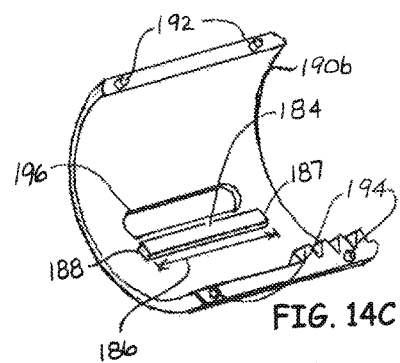
FIG. 14C
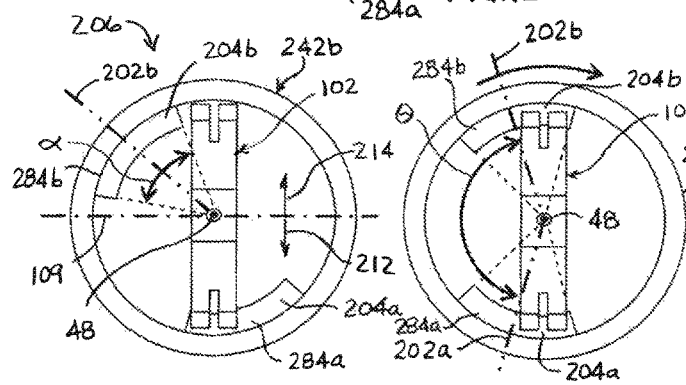
FIG. 13A  FIG. 13B  FIG. 13C
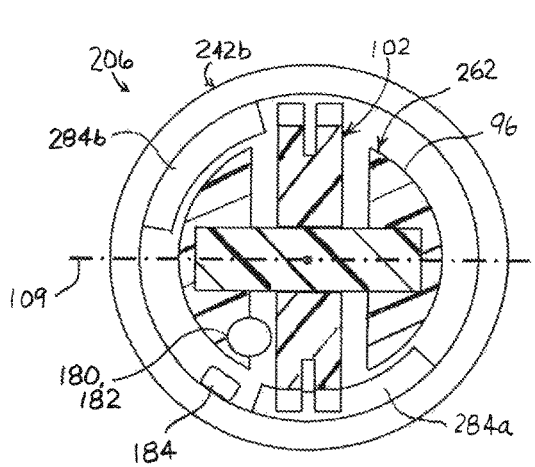 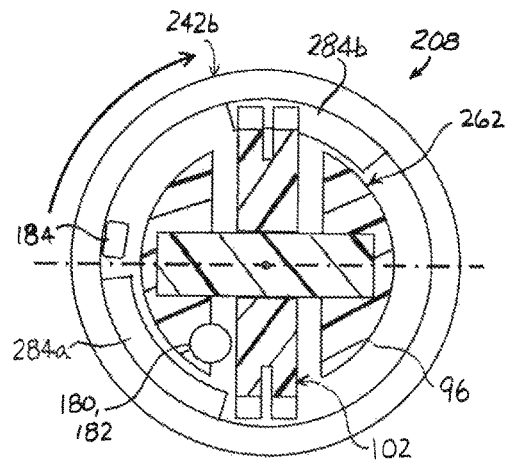
FIG. 14A  FIG. 14B

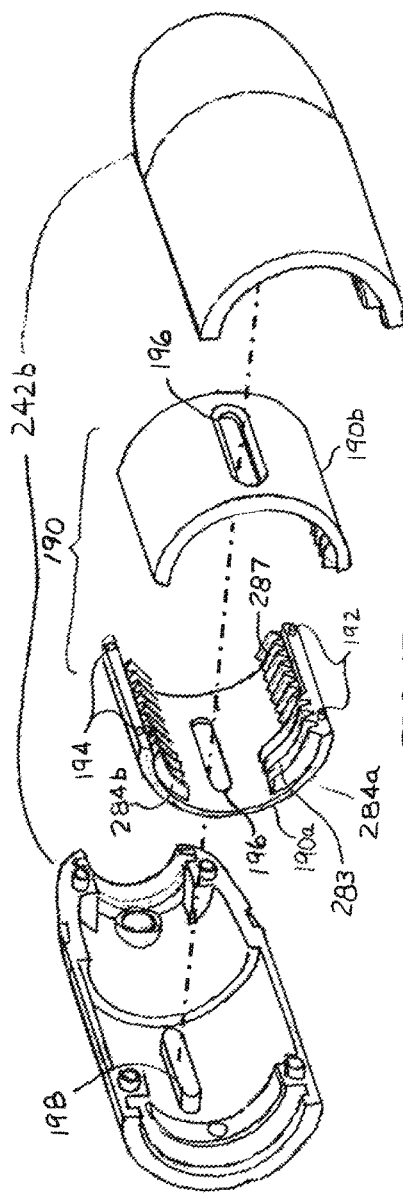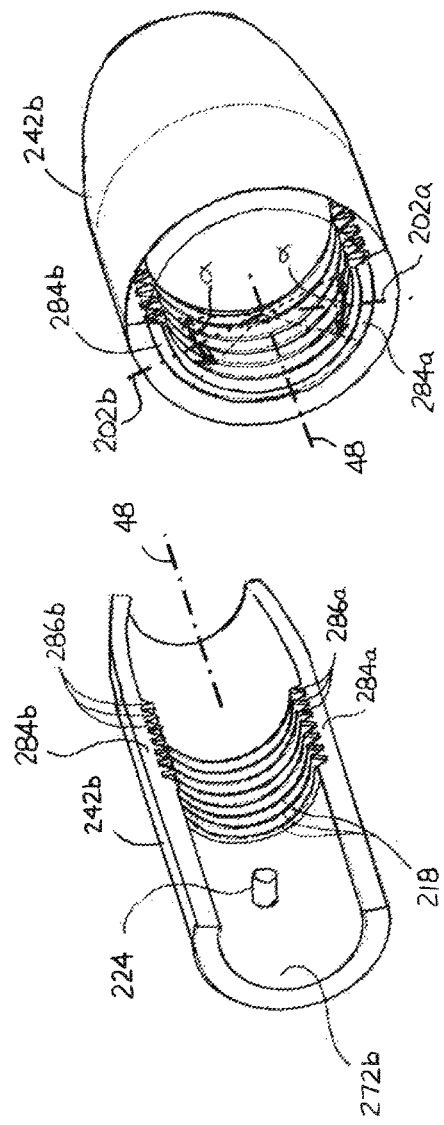

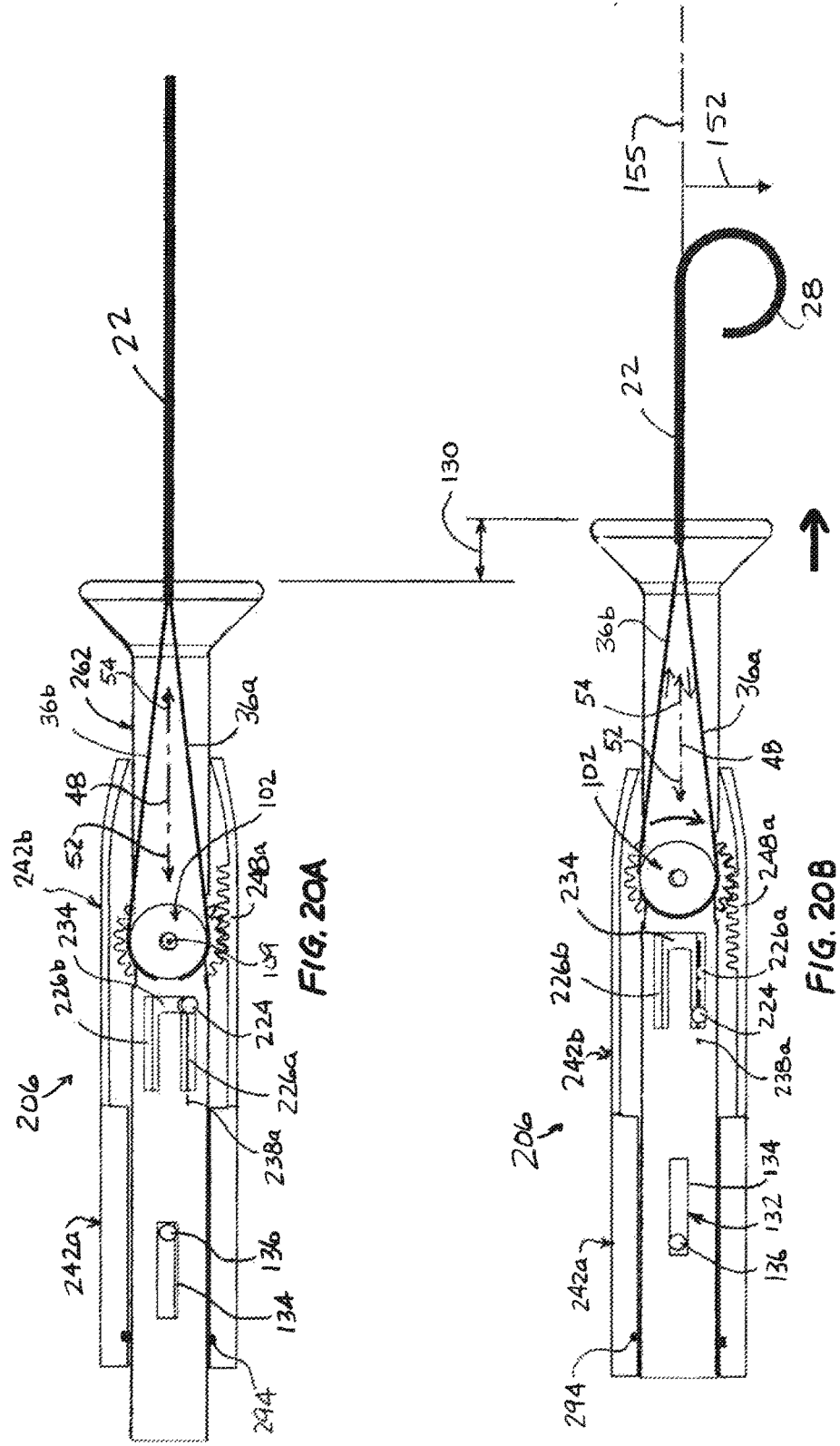

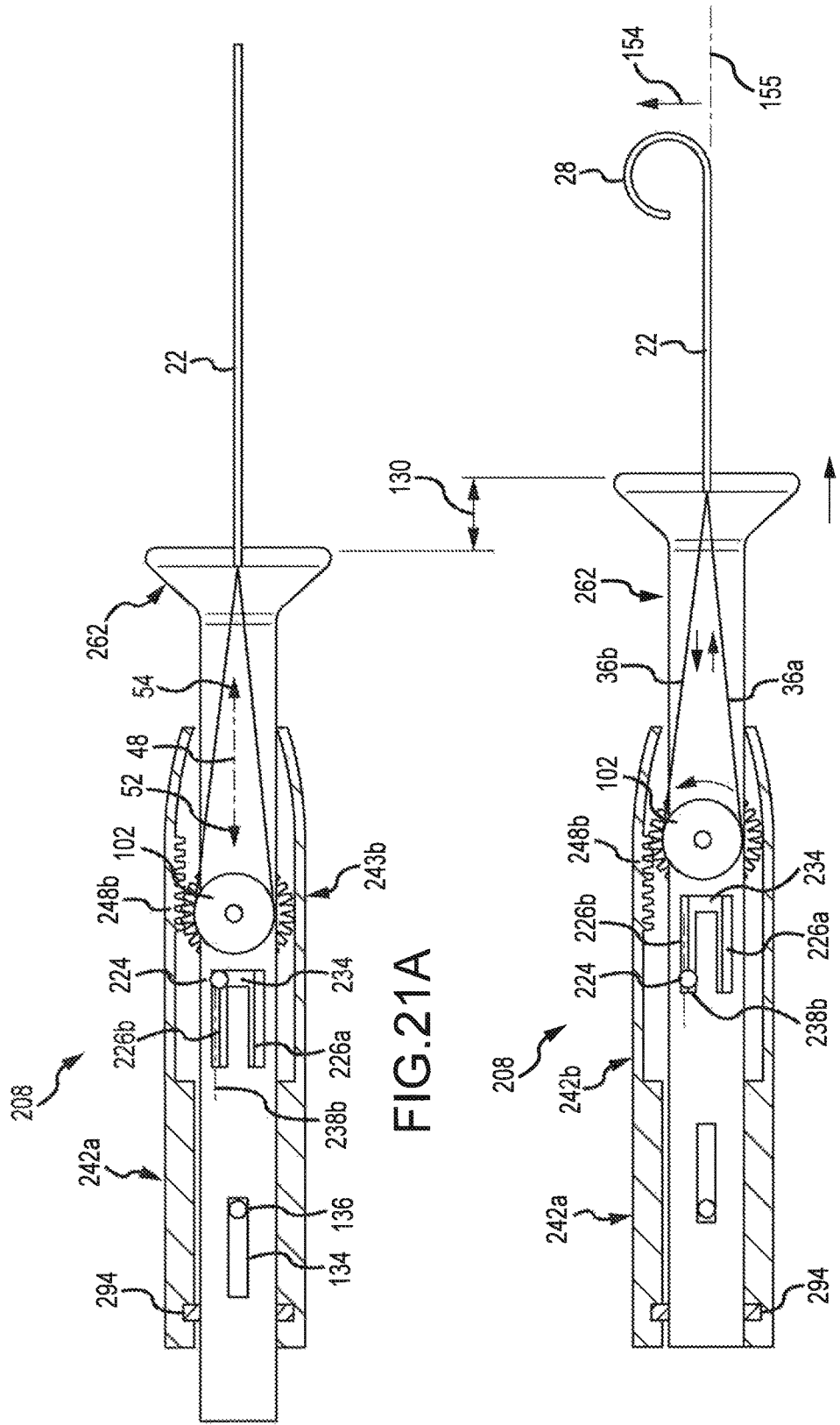

CONTROL HANDLES FOR CATHETERS

RELATED APPLICATION

This application is a continuation of U.S. Non-Provisional application Ser. No. 13/930,988, filed Jun. 28, 2013, and claims the benefit of U.S. Provisional Patent Application No. 61/817,661, filed Apr. 30, 2013, and U.S. Provisional Patent Application No. 61/819,335, filed May 3, 2013, the disclosures of which are hereby incorporated by reference in their entirety.

FIELD OF THE DISCLOSURE

The present disclosure is directed generally to handles for catheters, and more specifically to control handles for manipulating the distal end of catheters.

BACKGROUND

Various configurations of control handles exist for deflecting the distal end of a catheter. One form of control handle is the so-called "plunger type" handle that includes a generally cylindrical housing with a plunger extending therefrom. The operator generally grips the housing in the palm of a hand with four fingers and uses the thumb to translate the plunger forward and back relative to the housing along an actuation axis. A pull wire or wires are coupled to the plunger and housing in an arrangement that applies or releases tension in the pull wire(s) as the plunger is translated, thereby causing a controlled deflection of the distal tip of the catheter.

Many operators prefer the plunger type form of catheter control handle. Plunger type control handles do not have to be in a certain rotational orientation within the hand of the operator for operation. Thus, the plunger type handle can be rotated to affect rotation of the catheter body without need for the operator to twist the wrist and hand in uncomfortable positions in order to operate the handle. Also, the position of the plunger relative to the housing provides an indication of the degree of deflection occurring at the distal tip of the catheter. For bi-directional applications, one design challenge posed by the plunger type control handle providing balance between the amount of pull wire taken in and the amount of pull wire released by the control handle. That is, the amount of one wire end taken into the handle should generally be equal to the amount the other wire end released or let out of the handle. This has lead to rather elaborate designs including dual sliders or complicated routing within the handle to effect an equal amount of taken in and released wire.

A control handle that provides balanced intake and release of pull wire in the plunger type form with simplified internals would be welcome.

SUMMARY

Various embodiments of the disclosure include a hand held control handle of the plunger type form that provides a rotating spool for intake and release of a pull wire or pull wires. Spooling arrangements inherently release the same amount of wire as is taken in. Certain disclosed embodiments further include a switchable bi-directional control handle that provides the full stroke length of the plunger deflection in the selected lateral direction. Thus, the switchable bi-directional handle provides greater resolution in positioning the deflected tip of the catheter than state of the art plunger type handles that divide the plunger stroke between a first lateral direction and a second lateral direction. In one embodiment, each of the two lateral deflection directions is associated with a different bend radius.

The disclosed control handles can also be configured to prevent release of the spool during the switchover, thereby maintaining the neutral orientation of the catheter during the switchover.

The control handle can also include a biasing arrangement that affirmatively engages the handle for the selected tip deflection and prevents accidental switchover during catheter manipulation. In one embodiment, the control handle provides an output that informs a control system of the orientation of the control handle. This information can be utilized to inform the operator which direction of lateral deflection or which bend radius is being implemented at the distal tip of the catheter. The control handle can also be converted from a switchable handle to a non switchable handle, thus reducing or eliminating the need to keep inventories of separate parts for switchable and non-switchable control handles.

Structurally, in one embodiment of the disclosure, a control handle for a steerable catheter comprises a housing having a proximal portion and a distal portion and including an interior surface and an exterior surface, the interior surface defining a chamber surrounding an actuation axis. In this embodiment, the chamber is accessible from an opening defined on the distal portion of the housing, and the actuation axis defines a proximal direction and a distal direction. A plunger is disposed within the opening of the housing and having a proximal portion and a distal portion, the proximal portion of the plunger being disposed within the chamber, the distal portion extending distal to the opening. The plunger is translatable within the chamber along the actuation axis in the proximal and distal directions. A catheter body includes a proximal end portion and a distal end portion, the proximal end portion being attached to the distal portion of the plunger, the distal end portion of the catheter body including a steering section. A gear is disposed within the chamber and mounted to the plunger, the gear being rotatable about a rotation axis that is substantially perpendicular to the actuation axis. A spool portion is operatively coupled with the gear and rotatable about the rotation axis. At least one pull wire is engaged with the spool portion for collection about the rotation axis, the at least one pull wire extending from the spool portion through the distal portion of the plunger and the catheter body and being operatively coupled with the steering section of the catheter body. A gear rack is operatively coupled to the interior surface of the elongate chamber, the gear rack being in fixed relation with the interior surface of the elongate chamber, the gear being operatively coupled with the gear rack. In this embodiment, translation of the plunger relative to the housing along the actuation axis causes the gear rack to rotate the gear and the spool about the rotation axis. The spool portion can comprise a continuous tangential slot formed on the gear. The first gear rack can be integrally formed with the distal portion of the housing.

In another embodiment of the disclosure, a control handle for a steerable catheter comprises an elongate housing defining an opening on a distal end thereof, the elongate housing and the opening being concentric about an actuation axis, the actuation axis defining a proximal direction and a distal direction. In this embodiment, a plunger is disposed within the opening of the elongate housing and having a proximal portion and a distal portion, the proximal portion of the plunger being disposed within the elongate housing, with the distal portion extending distal to the opening of the elongate housing. The plunger is translatable within the elongate housing over a stroke length along the actuation axis. A catheter body can be attached to the distal portion of the plunger. A gear is mounted to the plunger and disposed within the elongate housing, the gear being rotatable about a rotation axis that is substantially perpendicular to the actuation axis. A spool portion is operatively coupled with the gear and rotatable about the rotation axis. At least one pull wire is engaged with the spool portion for collection about the rotation axis, the at least one pull wire extending from the spool portion through the distal portion of the plunger and into the catheter body. A first gear rack is operatively coupled with the elongate housing, the first gear rack being in fixed relation with the elongate housing. A second gear rack can be operatively coupled with and in fixed relation with the elongate housing.

The elongate housing can include a base section and a rotatable section, the rotatable section being rotatable about the actuation axis relative to the base section, the rotatable section including the first and second gear racks. The rotatable section is distal to the base section In certain embodiments, the control handle is selectively configurable in a first configuration to engage the first gear rack with the gear for rotation of the gear in a first rotational direction when the plunger is translated in the distal direction. The control handle can also be selectively configurable in a second configuration to engage the second gear rack with the gear for rotation of the gear in a second rotational direction when the plunger is translated in the distal direction, the second rotational direction being opposite the first rotational direction.

In one embodiment, the first and second gear racks extend radially inward from an interior surface of the elongate handle. The first and second gear racks can be formed on an insert that is operatively coupled with the elongate housing. The first gear rack and the second gear rack are defined by a common row of arcuate teeth that extend from the interior surface. The interior surface from which the first and second gear racks extend can be substantially cylindrical about the actuation axis. A portion of the first gear rack can be diametrically opposed to a portion of the second gear rack, so that both gear racks engage the gear and prevent release of the catheter assembly when switching between the first gear rack and the second gear rack. In one embodiment, each of the arcuate teeth define an arc that is greater than 180°.

Certain embodiments of the disclosure include a switching mechanism adapted to alternately switch the control handle between the first configuration and the second configuration. The switching mechanism can comprise a first guide slot and a switch pin, the switch pin being translated within the first guide slot when the plunger is translated along the actuation axis relative to the elongate housing. In one embodiment, the switch pin cooperates with the first guide slot to prevent rotation of the elongate housing about the actuation axis relative to the plunger over a portion of the stroke length of the plunger. The first guide slot can also maintain translational alignment between the gear and the first gear rack over a portion of the stroke length of the plunger. Likewise, the second guide slot can maintain translational alignment between the gear and the second gear rack over a portion of the stroke length of the plunger. In one embodiment, the first guide slot is formed on the plunger and the switch pin extends from the elongate housing. The switching mechanism can also comprise a second guide slot, the switch pin being switchable between the first guide slot and the second guide slot. The switch pin can be translated within the second guide slot when the plunger is translated along the actuation axis relative to the elongate housing. In one embodiment, the gear engages both the first gear rack and the second gear rack as the switch pin is switched between the first guide slot and the second guide slot.

A position indicating switch can be configured to close when the control handle is in the second configuration. In some embodiments, the position indicating switch is a reed switch.

In certain embodiments, the control handle further comprises a radial biasing element disposed on one of the elongate housing and the plunger. In this embodiment, the radial biasing element cooperates with one of a first axially extending groove and a second axially extending groove formed on the other of the elongate housing and the plunger, the radial biasing element being adapted to alternatively engage the first axially extending groove and the second axially extending groove to provide positive alignment of the switch pin with the first guide slot and the second guide slot, respectively.

In another embodiment of the disclosure, a method for deflecting a distal end of a catheter is disclosed, comprising:
providing a catheter operatively coupled to plunger-type catheter control handle, the plunger-type control handle including a plunger disposed in an elongate housing and including a first gear rack operatively coupled with the elongate housing and a gear rotatably mounted to the plunger, the plunger being translatable within the elongate housing along an actuation axis, the first gear rack being engageable with the gear, the gear being operatively coupled with a spool portion, the spool portion being operatively coupled with a pull wire for collection and release of the pull wire, the pull wire being operatively coupled with a distal end of the catheter for lateral deflection of the distal end of the catheter, wherein translation of the plunger in a first translational direction along the actuation axis causes the first gear rack to rotate the gear and the spool portion in a first rotational direction and to collect the pull wire on the spool, wherein translation of the plunger in a second direction along the actuation axis causes the first gear rack to rotate the gear and the spool portion in a second rotational direction and to release the pull wire from the spool;
providing instructions for operation of the catheter, the instructions including translating the plunger along the actuation axis in the first translational direction to deflect the distal end of the catheter in a first lateral direction.

The instructions can be included on a tangible medium, such as ink on paper or a computer-based file provided by the manufacturer, or conveyed orally by a manufacturer's representative.

The method can further comprise:
providing the catheter with a second gear rack operatively coupled with the elongate housing, the second gear rack being engageable with the gear, and a switching mechanism on the plunger-type control handle, the switching mechanism being configurable in a first configuration wherein the first gear rack is engaged with the gear, the switching mechanism being configurable in a second configuration wherein the second gear rack is engaged with the gear, wherein, when the switching mechanism is in the second configuration, translation of the plunger in the first translational direction along the actuation axis causes the second gear rack to rotate the gear and the spool portion in the second rotational direction and to release the pull wire from the spool, wherein translation of the plunger in the second direction along the actuation axis causes the second gear rack to rotate the gear and the spool portion in the first rotational direction and to collect the pull wire on the spool;

providing further instructions for operation of the catheter, the instructions including switching the switching mechanism to the second configuration and translating the plunger along the actuation axis in the first translational direction to deflect the distal end of the catheter in a second lateral direction such that said distal end of the catheter defines a curve, the second lateral direction being opposite the first lateral direction.

BRIEF DESCRIPTION OF THE DRAWINGS

FIG. 12 is a partial cutaway view of the catheter of FIG. 10 perpendicular to the actuation axis in an embodiment of the disclosure;

FIGS. 13A through 13C are partial sectional views of the catheter handle of claim 10, depicting the rotational progression when switching from a first rotational orientation to a second rotational orientation;

FIGS. 14A and 14B are partial sectional views of the catheter handle of claim 10, depicting a position indication sensing arrangement in an embodiment of the disclosure;

FIG. 14C is a perspective view of an insert portion having an elongate magnet mounted thereon;

FIG. 15 is an exploded view of the rotatable housing with a gear rack insert in an embodiment of the disclosure;

FIG. 16 is a cutaway view parallel to the actuation axis of a housing of a catheter handle having a row of arcuate teeth that define an angle greater than 180° an embodiment of the disclosure;

FIG. 17 is a partial cutaway view of the catheter of FIG. 16 perpendicular to the actuation axis in an embodiment of the disclosure;

FIGS. 20A and 20B are sectional views of the control handle of FIG. 10 during operation in a first rotational orientation in an embodiment of the disclosure; and FIGS. 21A and 21B are sectional views of the control handle of FIG. 10 during operation in a second rotational orientation in an embodiment of the disclosure.

DETAILED DESCRIPTION

Figure 1:
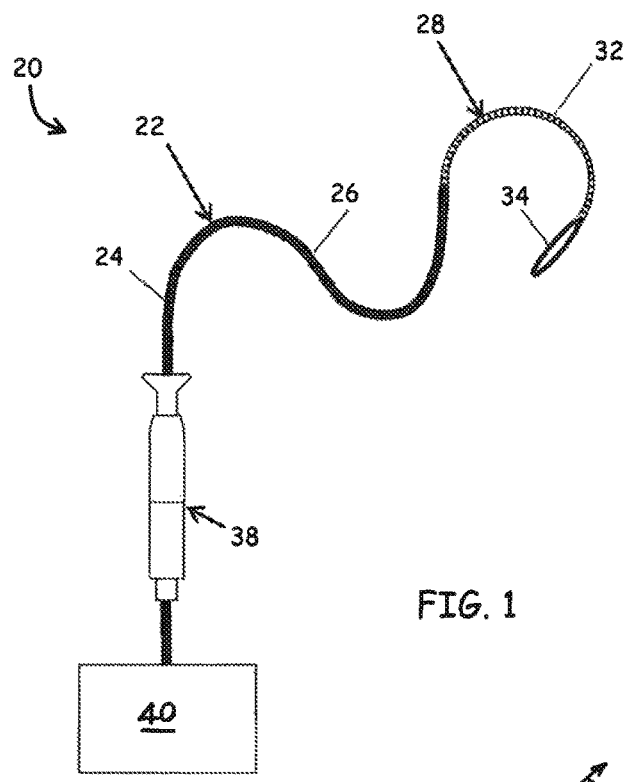
FIG. 1 is a catheter system in an embodiment of the disclosure.
Figure 3:
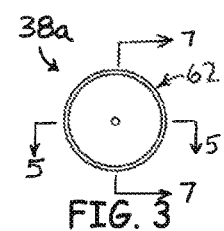
FIGS. 2 through 4 are views of a plunger type control handle in a first embodiment of the disclosure.
Figure 2:
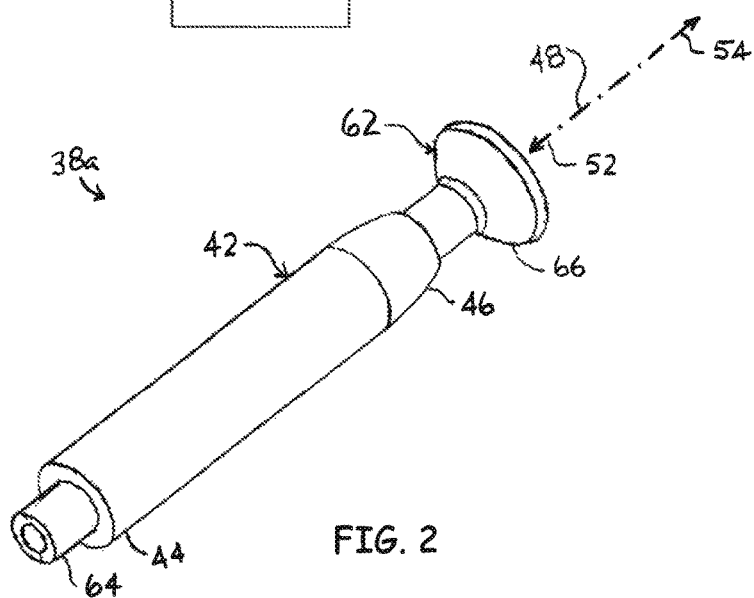
Figure 4:
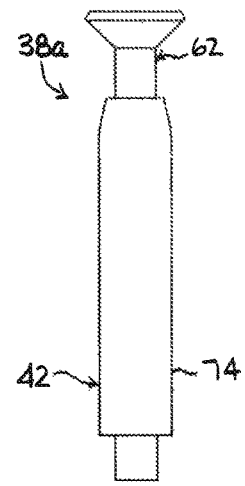

Referring to FIG. 1, a catheter system 20 is depicted in a disclosed embodiment. The catheter system 20 comprises an elongated catheter assembly 22 having a proximal portion 24, a middle portion 26 and a distal portion 28. The distal portion 28 of catheter assembly 22 includes a steering section 32, and can also include an end effector 34. The catheter system 20 can be equipped with instrumentation for determination of at least one operating condition of catheter assembly 22. Examples of operating parameters upon which the operating condition can be predicated includes a force, a temperature, a time interval (e.g., a duration or delay), and/or a flow (e.g., irrigation flow). In some embodiments, the instrumentation is disposed in end effector 34.

The steering section 32 further comprises one or more pull wires 36 (depicted in the various figures) disposed within elongated catheter assembly 22 and affixed to the distal end of steering section 32, wherein applying a pulling force to one of the at least one pull wires 36 causes steering section 32 to deflect. In one embodiment, the steering section 32 comprises a steering spine (not depicted). In other embodiments, the steering section 32 comprises a series of jointed segments or a flexible tube (neither depicted).

The proximal portion 24 is operatively coupled with a plunger-type control handle 38 for manipulating the pull wire(s) 36. The control handle 38 can be operatively coupled with a controller 40 containing various appurtenances that augment the operation of the catheter system 20. Non-limiting examples of the appurtenances of controller 40 include power sources and/or irrigation systems for sourcing the end effector 34, optical sources for sourcing fiber optic systems within the catheter system 20, data acquisition devices for monitoring instrumentation of the catheter system 20, and/or control systems for controlling the sourcing of the end effector 34. The controller 40 can be configured to receive input signals from the catheter assembly 22 and to produce output signals to catheter assembly 22. The controller 40 can be coupled to control handle 38 via instrumentation leads, power source leads, irrigation lines, fiber optics and/or wireless transmission.

In some embodiments, the instrumentation can include a force sensing assembly contained within or operatively coupled with end effector 34 for detection of contact force between an organ or vessel and end effector 34. Non-limiting examples of force sensing assemblies are disclosed at U.S. Patent Application Publication No. 2009/177095 to Leo et al., U.S. Pat. Nos. 8,075,498, 8,157,789, 8,182,433 and U.S. Pat. No. 8,298,227 to Leo et al., and U.S. Pat. No. 8,048,063 to Aeby et al., all of which are assigned to owner of the instant patent application, and the disclosures of which are hereby incorporated by reference in their entirety herein except for express definitions contained therein.

In another example, end effector 34 can be fitted with an ablation head coupled to an energy source (not depicted). The energy source can be located within the controller 40. In some embodiments, controller 40 can include analog electronic components to execute the control logic required to monitor operational parameters. In still other embodiments, the controller 38 includes both analog and digital components for this purpose. The controller 40 can comprise a general purpose computer, or a specialized console configured for operation only with catheter system 20.

Referring to FIGS. 2 through 8, a control handle 38*a* is depicted in a disclosed embodiment. The control handle 38*a* includes a housing 42 having a proximal end portion 44 and a distal end portion 46 and defining an actuation axis 48 passing through the proximal and distal end portions 44 and 46. A proximal translational direction 52 and a distal translational direction 54 are defined along the actuation axis 48. A plunger assembly 62 is disposed in the control handle 38*a*, the plunger assembly 62 having a proximal end portion 64 and a distal end portion 66, the plunger assembly 62 being translatable within the housing 42 along the actuation axis 48. In the depicted embodiment, the actuation axis 48 passes through the proximal and distal portions 64 and 66 of the plunger assembly 62.

The housing 42 includes an interior surface 72 and an exterior surface 74 and defines a distal opening 76 at the distal end portion 46 that provides access to an elongate chamber 78 surrounding the actuation axis 48, the boundaries of the elongate chamber 78 being defined by the interior surface 72 of the housing 42. In some embodiments, the elongate chamber 78 is concentric about the actuation axis 48. In one embodiment, the housing 42 defines a proximal opening 82 at the proximal end portion 44. The housing 42 further includes a gear rack 84 comprising a plurality of teeth 86 that extend from the interior surface 72. The plurality of teeth 86 protrude toward the actuation axis 48 and are arranged sequentially in the proximal and distal translational directions 52 and 54. In one embodiment, the gear rack 84 is integrally formed on the interior surface 72 of the housing 42.

The plunger assembly 62 includes a plunger 92 with a knob portion 94 and a body portion 96 that extends from the knob portion 94, the body portion including an exterior surface 98. In the depicted embodiment, the knob portion 94 is located distal to the body portion 96. A gear 102 having a plurality of teeth 104 is operatively coupled to the body portion 96 of the plunger 92. The gear 102 can be mounted to an axle 106 that passes through gear 102, each of the opposing ends of the axle 106 being mounted within respective apertures 108 formed in the body portion 96. The axle 106 defines a rotational axis 109 about which the gear 102 rotates, the rotational axis 109 being substantially orthogonal to the actuation axis 48. In one embodiment, the gear 102 rotates about the axle 106. In other embodiments, the axle 106 is in a fixed relation with the gear 102 (e.g., press fit, keyed, axle 106 and gear 102 integrally formed), with the axle 106 rotating within the apertures 108.

The gear 102 can include a spooling arrangement comprising a spool portion 112 that is integral with the gear 102. The spool portion 112 can comprise a continuous tangential slot. 11.4 that is laterally centered on the gear 102, the tangential slot 114 extending radially inward, into or through the teeth 104 of the gear 102 to define a spool radius 116. In the depicted embodiment, pull wire end portions 36*a* and 36*b* are anchored to the spool portion 112 within the tangential slot 114, and "spool" about the spool radius 116 (i.e., are alternatively collected and released). For bi-directional control, the pull wire end portions 36*a* and 36*b* are wrapped in complementary fashion about the spool portion 112. That is, in the view presented in FIG. 7, pull wire end portion 36*a* is wrapped counterclockwise about the rotational axis 109 when going from proximal to distal, whereas pull wire end portion 36*b* is wrapped clockwise about the rotational axis 109 when going from proximal to distal.

Figure 5:
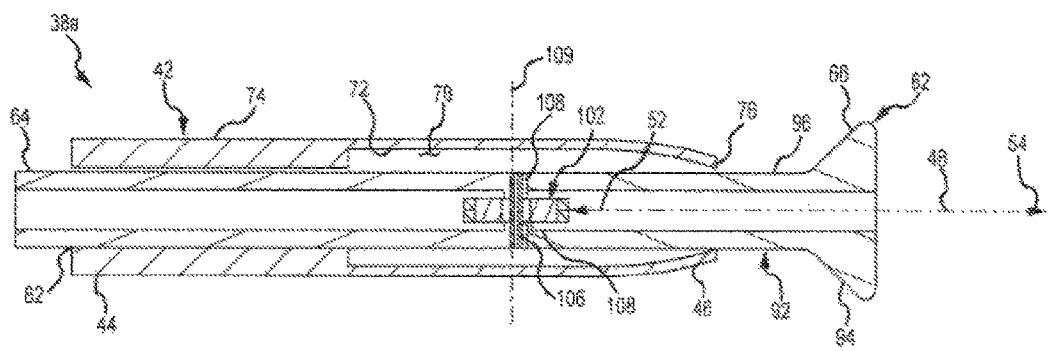
FIG. 5 is a sectional view of the control handle of FIGS. 2 through 4 in an embodiment of the disclosure.
Figures 5A, 6A:
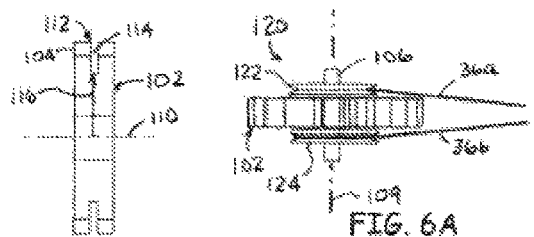
FIG. 5A is an integrated gear and spool of the control handle of FIG. 5 in an embodiment of the disclosure.
FIGS. 6A and 6B are orthogonal projections of an alternative spooling arrangement in an embodiment of the disclosure.
Figure 6B:

Referring to FIGS. 6A and 6B, an alternate spooling arrangement 120 is depicted in a disclosed embodiment. In the depicted embodiment, the spooling arrangement 120 includes two spool portions 122 and 124, each coupled to a respective side of the gear 102. Two pull wire end portions 36*a* and 36*b* can be coupled to the spool portions 122 and 124, respectively, and wrapped in opposite directions about the rotational axis 109. For example, in the view presented in FIG. 6B, pull wire end portion 36*a* is wrapped counterclockwise about the rotational axis 109 when going from proximal to distal, whereas pull wire end portion 36*b* is wrapped clockwise about the rotational axis 109 when going from proximal to distal. Accordingly, the spool portions 122 and 124 are not laterally centered within the gear 102 for the spooling arrangement 120.

Functionally, the complementary wrapping of the pull wire end portions 36*a* and 36*b* of both the spooling arrangements 110 and 120 enable one end portion to be gathered by the spool portion(s) while the other is simultaneously released by the spool portion(s). For the circular spool portion(s) having the same radius, the amount of pull wire end portion 36*a* released or gathered by the spool portion(s) will be substantially the same as the amount of pull wire end portion 36*b* gathered or released by the spool portion. In this way, when one pull wire end portion is placed in tension, the other is released so that the spooling arrangements 110 and 120 do not cause competing tension stress at the steering section 32.

While two pull wire end portions 36*a* and 36*b* are depicted, it is understood that the control handles 38 depicted herein are not limited to spooling only two pull wire end portions. Alternatively, it is contemplated that a single pull wire end portion 36*a* or 36*b* can be utilized for unidirectional deflection, or that a single pull wire can be wrapped around the spool portion 112 with two opposing ends extending into the catheter assembly 22. It is farther noted that the two pull wire end portions 36*a* and 36*h* can be two ends of the same pull wire 36 that is looped within the catheter assembly 22.

The gear 102 and the gear rack 84 are arranged so that the teeth 104 of the gear 102 are engaged with the teeth 86 of the gear rack 84 throughout a stroke length 130 of the plunger assembly 62. The control handle 38*a* can also include a stop mechanism 132 comprising an elongate slot 134 formed on the body portion 96 of the plunger 92 and a stop pin 136 that extends radially inward from the interior surface 72 of the housing 42 into the elongate slot 134.

Figure 7:
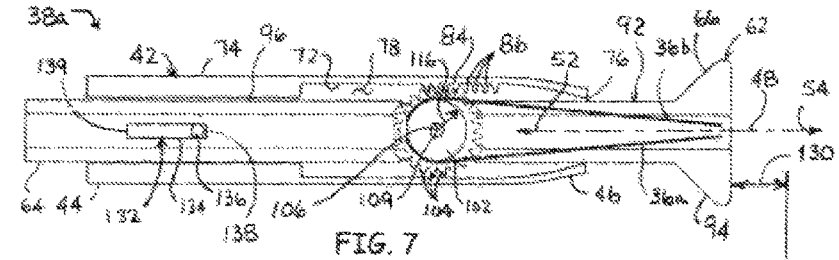
FIGS. 7 and 8 are sectional views orthogonal to the sectional view of FIG. 5 with the plunger fully retracted and fully extended, respectively, in an embodiment of the disclosure.
Figure 8:
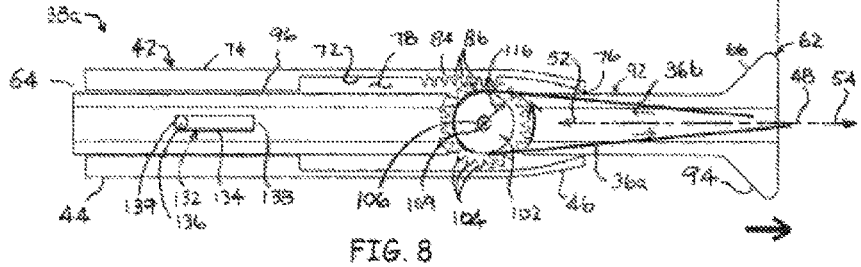

Functionally, the elongate slot 134 and the stop pin 136 can cooperate to limit the stroke length 130 of the plunger 92 along the actuation axis 48, to prevent damage to the internal components and/or to prevent the gear 102 from running off the gear rack 84 in the proximal or distal translational directions 52 or 54. In the depicted embodiment, when the plunger 92 is fully retracted in the proximal translational direction 52, the stop pin 136 engages a distal end 138 of the elongate slot 134 (FIG. 7); when the plunger 92 is fully extended in the distal translational direction 54, the stop pin 136 engages a proximal end 139 of the elongate slot 134 (FIG. 8). The stop mechanism can also prevent rotation of the plunger 92 relative to the housing 42 about the actuation axis 48, thereby maintaining tangential alignment between gear rack 84 and the gear 102.

In one embodiment, the control handle 38a includes a resistance adjustment assembly (not depicted) between the piston assembly 62 and the housing 42 That can be adjusted to provide the desired frictional characteristics of the user for control of the resistance between the piston assembly 62 and the housing 42. In one embodiment, the piston assembly is configured to provide a frictional resistance that varies dynamically to substantially match the restorative force across the range of catheter tip deflection. A frictional resistance adjustment assembly suitable for implementation into the control handles 38 described herein is disclosed in U.S. Patent Application Publication No. 2011/0251554 to Romoscanu, owned by the owner of the present application, and the disclosure of which is hereby incorporated by reference herein except for express definitions contained therein.

In operation, the plunger assembly 62 is translated within the housing 42 along the actuation axis 48. The translation of the plunger assembly 62 moves gear 102 translationally relative to the gear rack 84, thereby causing the gear 102 to rotate about the rotation axis 109. From the perspective of the FIGS. 7 and 8 illustrations, translating the plunger assembly 62 in the distal direction 54 causes the gear 102 to rotate counterclockwise (as depicted). Rotation of the gear 102 causes the pull wire end portion 36b to collect on the spool portion 112 and the pull wire end portion 36a to be let out by the spool portion 112 in substantially equal amounts. Conversely, translating the plunger assembly 62 in the proximal translational direction 52 rotates the gear 102 clockwise, causing the pull wire end portion 36a to collect and the pull wire end portion 36b to be let out.

Figure 9A:
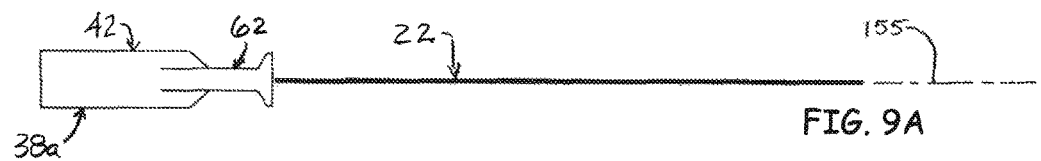
FIGS. 9A through 9C depicts the operation of the plunger type control handle of FIGS. 2 through 8 in an embodiment of the disclosure.
Figure 9B:
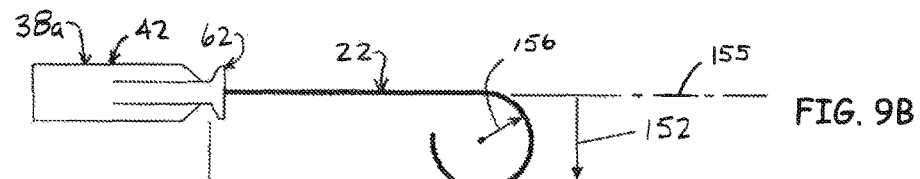
Figure 9C:
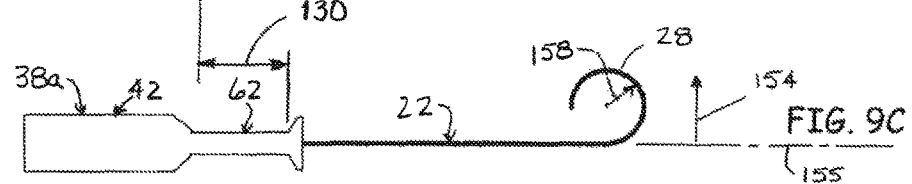
Figure 10:
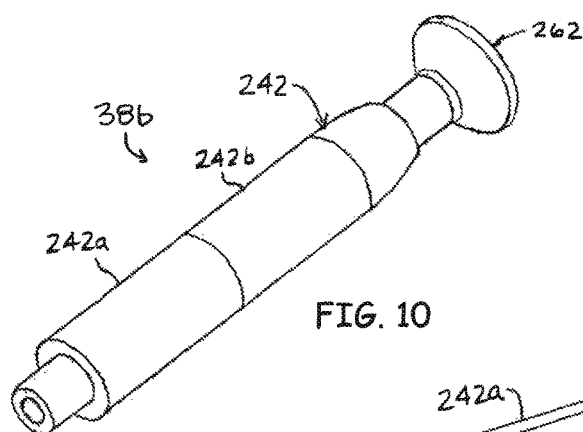
FIG. 10 is a perspective view of a switchable, bi-directional catheter handle in a second embodiment of the disclosure.

Referring to FIGS. 9A through 9C, the catheter assembly 22 as operated by the control handle 38a in a bi-directional manner is depicted in an embodiment of the disclosure. In this embodiment, the catheter assumes a "neutral" position (i.e., no control handle-induced curvature) when the plunger assembly 62 is at a mid-stroke position, as depicted in FIG. 9A. Retracting the piston assembly 62 into the housing 42 (i.e., translating the piston assembly 62 in the proximal translational direction 52 relative to the housing 42) causes the pull wire end portion 36b to be collected on the spool portion 112, placing the pull wire end portion 36b in tension and causing the steering section 32 to deflect the distal portion 28 in a first lateral direction 152 (FIG. 9B). Extending the piston assembly 62 further out of the housing 42 (i.e., translating the piston assembly 62 in the distal direction 54 relative to the housing 42) causes the pull wire end portion 36a to be collected on the spool portion 112, placing the pull wire end portion 36a in tension which is transferred to the steering section 32 and causing the distal portion 28 to deflect in a second lateral direction 154 (FIG. 9C). Herein, the first and second lateral directions are normal to a longitudinal axis 155 of the catheter assembly 22. In one embodiment, two different radii of curvature 156 and 158 are imposed on the steering section 32 in the first and second lateral directions 152 and 154, respectively. A catheter assembly having two different radii of curvature is disclosed in U.S. Patent Application No. 61/819,216 owned by the owner of the instant application an filed on even date herewith, the disclosure of which is hereby incorporated by reference herein in its entirety except for express definitions contained therein.

Referring to FIGS. 10-21, a bi-directional switchable control handle 38b is depicted in disclosed embodiments. The control handle 38b includes a housing 242 and a plunger assembly 262 having many of the same components as the housing 42 and plunger assembly 62 of the control handle 38b, some of which are identified with like-numbered numerical references in FIGS. 10-21.

The housing 242 includes two housing components: a stationary housing portion 242a and a rotatable housing portion 242b, each characterized as having an interior surface 272a and 272b, respectively (referred to collectively as interior surfaces 272). The housing 242 further includes a first gear rack 284a and a second gear rack 284b (referred to collectively as gear racks 284), each having a plurality of gear rack teeth 286a and 286b, respectively. The gear racks 284 are disposed within the housing 242 and in a fixed relationship relative to the interior surface 272b of the rotatable housing portion 242b.

In one embodiment, the gear rack teeth 286a, 286b of each gear rack 284a. 284b are arcuate about the actuation axis 48 and having a tangential arc segment α (FIGS. 13A and 13C). Each of the gear racks 284a and 284b can be characterized as being centered about a respective median plane 202a and 202b, each of the median planes 202a and 202b passing through the actuation axis 48. The median planes 202a and 202b are rotationally offset from each other by an obtuse angle θ (FIG. 13B), the angle θ being less than 180°. In one embodiment, while the median planes 202a and 202b are not diametrically opposed, there are portions of the gear racks 284a and 284b that are diametrically opposed, denoted by numerical references 204a and 204b, respectively.

In operation, the gear racks 284 are arranged to selectively engage the gear 102, as depicted in FIGS. 12 and 13A-13C. With the rotatable housing portion 242b in a first rotational orientation 206 about the actuation axis 48 (FIGS. 12 and 13A), the first gear rack 284a is engaged with a portion of the gear 102 that is located in a first direction 212 relative to the rotational axis 109. In this first rotational orientation 206, the second gear rack 284b is rotationally positioned away from the gear 102 and does not engage the gear 102.

The rotatable housing portion 242b can then be rotated about the actuation axis 48 (FIG. 13B) to a second rotational orientation 208 (FIG. 13C), so that the first gear rack 284a is rotated out of engagement with the gear 102 while the second gear rack 284b is rotated into engagement with the gear 102 (FIG. 13C). Engagement of the second gear rack 284b occurs on a portion of the gear 102 that is located in a second direction 214 relative to the rotation axis 109, the second direction 214 being opposite the first direction 212.

In one embodiment, both the first gear rack 284a and the second gear rack 284b engage the gear 102 during the transition from the first rotational orientation 206 to the second rotational orientation 208, as depicted in FIG. 13B. That is, during the transition from the first rotational orientation 206 to the second rotational orientation 208, the diametrically opposed portions 202a and 202b of the gear racks 284a and 284b simultaneously engage the gear 102.

In one embodiment, the gear rack teeth 286a, 286b of each gear rack 284a, 284b include a combination of arcuate teeth 283 and straight teeth 287, with the arcuate teeth 283 comprising the proximal portion of the gear rack 284a, 284b and the straight teeth comprising the distal portion of the gear rack 284a, 284b. In one embodiment, the arcuate teeth 283 are of greater tangential dimension that the straight teeth 285.

Functionally, the arcuate shape and larger tangential dimension of the arcuate teeth 283 facilitate a smooth switchover depicted at FIGS. 13A through 13C. During the switchover, the steering section 32 of the catheter assembly 22 is in the "neutral" position, so that the load imposed on arcuate teeth 283 is less than when the catheter assembly 22 is in a deflected position. Accordingly, arcuate teeth 283 can engage the straight gear teeth 104 of the gear 102 without causing damage to the gear racks 284 or the gear teeth 104. The straight teeth 287 engage the gear 102 as the piston assembly 262 is extended in the distal direction 54, i.e., when steering section is in a deflected state. Thus, the straight teeth 287, which are not arcuate, engage the straight gear teeth 104 more fully than do the arcuate teeth 283, and where the mechanical transfer of force between the gear 102 and the gear racks 284 are the greatest. The better engagement under heavier load militates against damage to the gear racks 284 and the gear teeth 104. Also, the straight teeth 287 of the gear teeth 286a, 286b do not have to cover the same tangential dimension as the arcuate teeth 283 because there is no switchover operation performed when the gear 102 is engaged with the straight teeth 287.

Referring to FIGS. 14A and 14B, a position indicating switch 180 is depicted in a disclosed embodiment. In the depicted embodiment, the position indicating switch 180 is a magnetic reed switch 182 that is activated by a magnet 184. The magnetic reed switch 182 is mounted to the body portion 96 of the plunger 92, while the magnet 184 is operatively coupled to the rotatable housing portion 242b (i.e., mounted to the interior surface 272b or to the insert 190, discussed below, which follows the rotatable housing portion 242b).

The magnet 184 is arranged to be in close proximity to the magnetic reed switch 182 when the switchable bi-directional control handle 38a is in the first rotational orientation 206 (FIG. 14A), thereby activating the magnetic reed switch 182. To assure that closure of the magnetic reed switch 182 is maintained throughout the full stroke length 130 of the piston assembly 62, the magnet 184 can be elongate, as depicted in FIG. 14C, and arranged and having a dimension 186 so that a distal end 187 of the magnet 184 is proximate the magnetic reed switch 182 when the piston assembly is fully extended, and a proximal end 188 is proximate the magnetic reed switch 182 when the piston assembly 62 is full retracted.

Upon rotation to the second rotational orientation 208, the magnet 184 is rotationally removed from the sensing proximity of the magnetic reed switch 182, thus deactivating the magnetic reed switch 182.

The position indicating switch 180 (e.g., reed switch 182) can be operatively coupled to the controller 40. Upon activation and/or deactivation of the position indicating switch 180, the controller 40 can provide the user with an indication of the orientation of the bi-directional switchable control handle 38h (e.g., an indication that the "large curvature radius" or the "small curvature radius" is currently activated).

A non-limiting example of a magnetic reed switch 182 is the model MK20/1-C-100W, provided by Meder Electronic AG of Singen, Germany. A non-limiting example of a material for magnet 184 is neodymium supermagnet, manufactured by Supermagnete of Gottmadingen, Germany.

Figure 11:
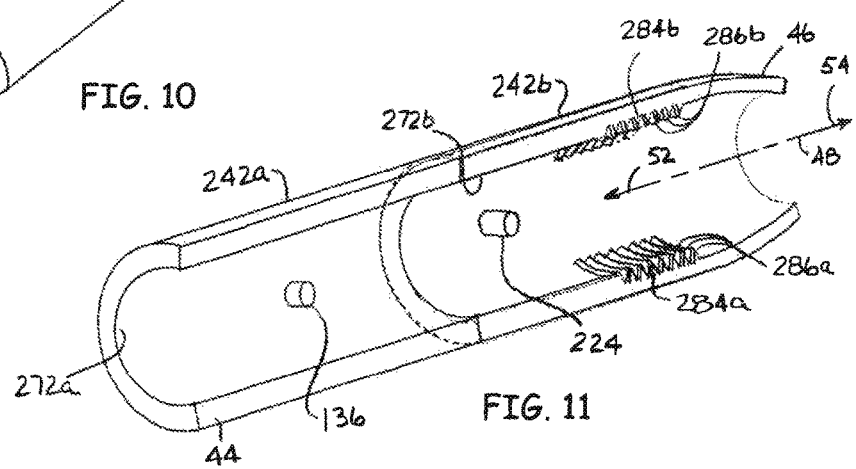
FIG. 11 is a cutaway view parallel to the actuation axis of the housing of the catheter handle of FIG. 10 in an embodiment of the disclosure.

The gear racks 284 can be formed from integrally with the rotatable housing portion 242b, as depicted in FIGS. 11 and 12, or they can be formed separately as part of an insert 190, as depicted in FIG. 15. The insert 190 can be formed in two portions 190a and 190b that include pins 192 and recesses 194 that mate together to form the insert 190. In one embodiment, the insert 190 includes one or more mounting apertures 196 that align with a corresponding number of mounting blocks 198 that project radially inward from the interior surface 272h of the rotatable housing portion 242b. In the depiction of FIG. 15, the rotatable housing portion 242b is bifurcated.

Functionally, the mounting block(s) 198 and mounting aperture(s) 196 cooperate to retain the insert 190 in a fixed relationship relative to the rotatable housing 242b, both axially and rotationally. The bifurcation of the housing portion 242b insertion of the mounting block(s) 198 into the mounting aperture(s) 196. Bifurcation of the insert 190 into halves 190a and 190h can also facilitate assembly of the piston assembly 62 and rotatable housing portion 242b.

In one embodiment, the gear rack teeth 286a and 286b can be formed from a common row of arcuate teeth 218, as illustrated in FIGS. 14 and 15. It is understood that, while sharing a common row of extended arcuate teeth 218, there are still defined two gear racks 284a, 284h, each with a respective median plane 202a, 202b. In such an embodiment, the gear racks 284a and 284b are defined by the tangential arc segment α across which the teeth 104 of the gear 102 engage the extended arcuate teeth 218 during rotation from the first rotational orientation 206 to the second rotational orientation 208. Similarly, the median planes 202a and 202b are the planes that pass through the midpoint of the respective tangential arc segment α and include the actuation axis 48.

Figure 18:
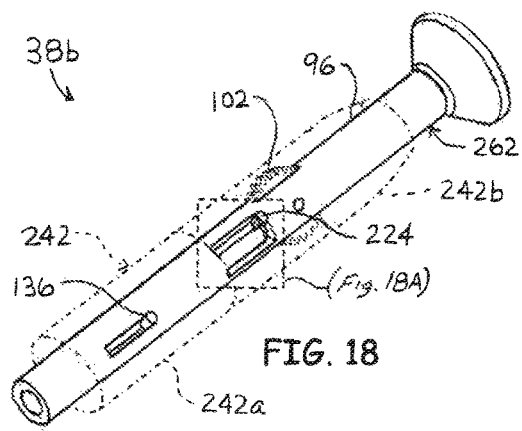
FIG. 18 is a perspective view of the plunger assembly of the catheter handle of FIG. 10 in an embodiment of the disclosure.
Figure 18A:
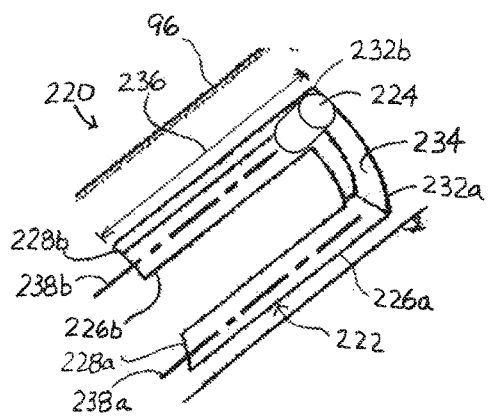
FIGS. 18A through 18C are enlarged views of various U-slot arrangements for the plunger assembly of FIG. 18 in embodiments of the disclosure.

In one embodiment, the bi-directional switchable control handle 38b further includes a switching mechanism 220 (FIGS. 18, 18A and 18B) to augment alignment of the gear racks 284. The switching mechanism 220 can comprise a U-shaped slot 222 formed on the body portion 96 of the plunger 92 and a switch pin 224 that extends radially inward into the U-shaped slot 222 from the interior surface 272b of the rotatable housing portion 242b. The switch pin 224 is depicted in isolation in FIGS. 18 and 18A-18C with the remainder of the housing 242 removed for clarity. The U-shaped slot 222 can be characterized as having a first guide slot 226a and a second guide slot 226b (referred to collectively as guide slots 226), each having a proximal end 228a, 228b and a distal end 232a, 232b and being connected by a lateral slot 234. The first and second guide slots 226a and 226b are parallel to each other, each having a major dimension 236 that defines a first guide axis 238a and a second guide axis 238b, respectively, the guide axes 238a and 238b extending parallel to the actuation axis 48. The lateral slot 234 extends tangentially between the guide slots 226. In the depicted embodiment, the lateral slot 234 connects the distal ends 232a and 232b of the guide slots 226a and 226b.

Figure 18B:
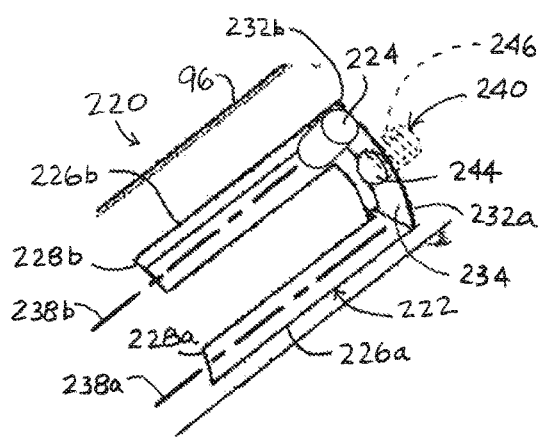

The switching mechanism 220 can also include an axial biasing element 240 operatively coupled to the lateral slot 234 (FIG. 18B). The axial biasing element 240 is so-named because it is oriented to apply a biasing force in the axial direction (i.e., parallel to the actuation axis 48). The axial biasing element 240 can comprise an engagement element 244, such as a spring loaded plunger or ball. The axial biasing element 240 can be disposed in a cavity 246 formed in the body portion 96 of the plunger 92 adjacent the lateral slot 234. The engagement element 244 can be arranged to extend partially into the lateral slot 234 and be capable of retracting into the cavity 246 upon exertion of an axial force on the engagement element 244.

Figure 18C:
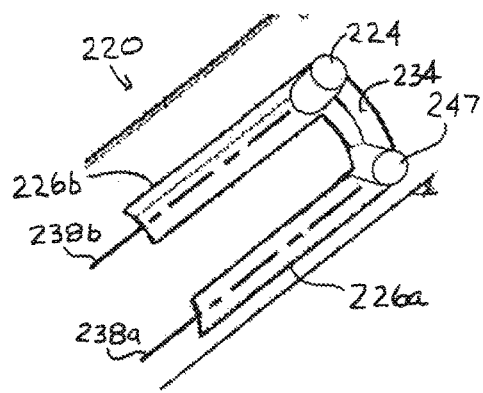

The bi-directional switchable control handle 38b can also be converted into a non-switchable control handle by altering the switching mechanism 220 as depicted in FIG. 18C. A second pin 247, depicted in isolation in FIG. 18C and also extending radially inward into the U-shaped slot 222 from the interior surface 272b of the rotatable housing portion 242b. The second pin 247 is rotationally spaced from the switch pin 224 so as to translate along the second guide axis 238b as the switch pin 224 translates along the first guide axis 238a.

Functionally, the ability to convert, the bi-directional switchable control handle 38b into a non-switchable control handle enables both handle types to be implemented from the same handle form, thereby reducing the need for separate inventories. The second pin 247 can be implemented numerous ways that require little in the way of additional tooling. For example, an orifice (not depicted) can be located in the rotatable housing 242b where the second pin 247 is to be positioned. The orifice could be filled with a plug that is flush with interior surface 272b of the rotatable housing portion 242b for a switchable handle, or with the second pin 247 pressed through the housing and into the U-shaped slot 222 to render the handle form non-switchable. In other embodiments, a modified version of the rotatable housing portion that includes the second pin 247 could be fabricated as an alternative component for non-switchable handles.

Figure 19:
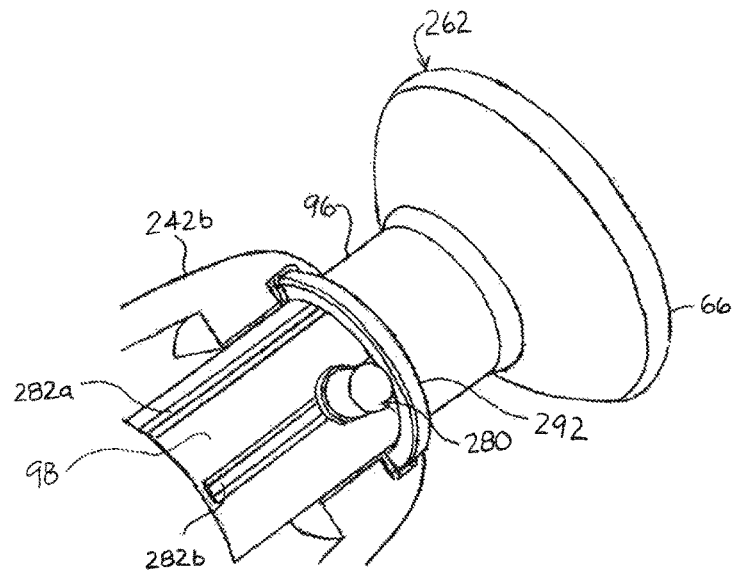
FIG. 19 is an enlarged cutaway view of the distal end of the control handle including a radial biasing arrangement for use in the control handle of FIG. 10 in an embodiment of the disclosure.
Figures 19A, 19B:
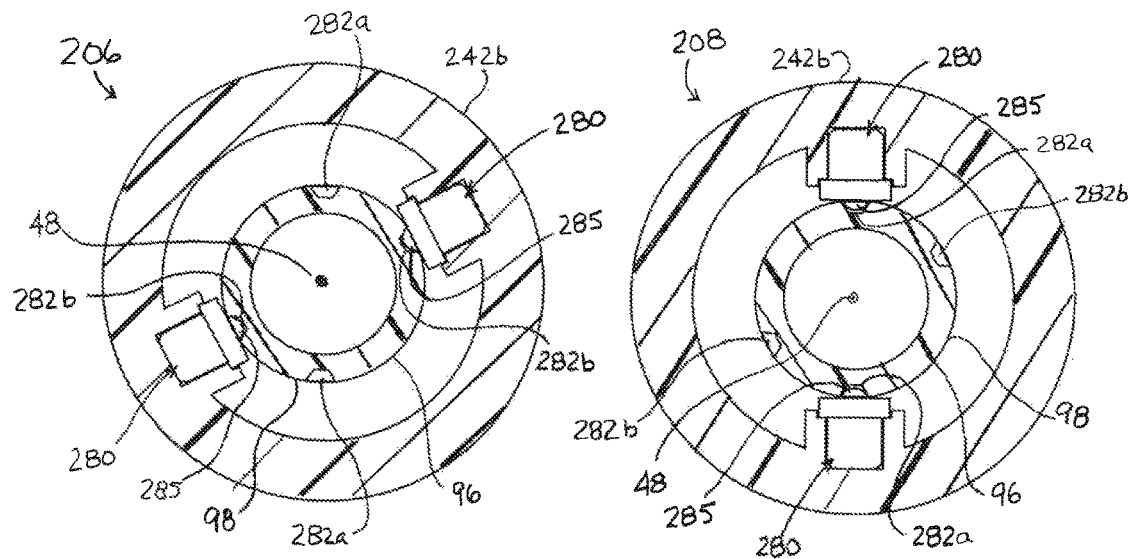
FIGS. 19A and 19B are enlarged sectional views of the radial biasing arrangement of FIG. 19 in an embodiment of the disclosure.

In an alternative biasing arrangement, at least one radial biasing element 280 is utilized for positively aligning the switch pin 224 with the respective guide slot 226a or 226b after switchover, as depicted in FIGS. 19, 19A and 19B (referred to collectively as FIG. 19). The radial biasing element 280 is so-named because it is oriented to exert a force along a radial axis (i.e., an axis substantially orthogonal to the actuation axis 48). In the FIG. 19 arrangement, at least one radial biasing element 280 is operatively coupled to the rotatable housing portion 242b and oriented to actuate radially inward (i.e., towards the actuation axis 48) to engage the exterior surface 98 of the body portion 96 of the plunger 92.

Like the axial biasing element 240, the radial biasing element 280 can include an engagement element 285, such as a spring loaded ball or plunger. For each radial biasing element 280, the body portion 96 of the plunger 92 includes first and second axially extending grooves 282a and 282b that can be selectively engaged with the respective radial biasing element 280. The radial biasing element 280 and the first axially extending groove 282a are arranged so that when the switch pin 224 is aligned with guide axis 238a, the radial biasing element 280 is aligned over and registered within the first axially extending groove 282a. Likewise, the radial biasing element 280 and the second axially extending groove 282b are arranged so that when the switch pin 224 is aligned with guide axis 238b, the radial biasing element 280 is aligned over and registered within the second axially extending groove 282b.

In an alternative arrangement, the radial biasing element 280 can be mounted to the body portion 96 of the plunger 92 and oriented to exert a force radially outward from the actuation axis 48 for engagement with axially extending grooves formed on the interior surface 272b of the rotatable housing portion 242b (not depicted).

In one embodiment, the biasing force exerted by the radial biasing element 280 can be sufficient to require deliberate action to disengage the radial biasing element 280 from the axially extending groove 282a or 282b. That is, the force exerted by the one or more radial biasing element(s) 280 is substantial enough to require the operator to grip the stationary housing portion 242a in one hand and the rotatable housing portion 242b in another hand in order to exert a torsion force sufficient to cause the radial biasing element(s) 280 to disengage with the axially extending groove 282a or 282b. A nonlimiting example of the biasing force provided by the radial biasing element(s) 280 to effect this functionality is about 0.6 kg. Functionally, the substantial biasing force prevents the rotatable housing 242b from being inadvertently rotated with respect to the stationary housing 242a while the steering section 32 is being manipulated.

In one embodiment, the control handles 38a and 38b (referred to generically as control handles 38) include a distal end bushing 292 mounted at the distal end portion 46 of the housing 42 or 242 (FIG. 19). A proximal end bushing 294 can also be mounted at the proximal end portion 44 of the housing 42 or 242 (FIGS. 20A and 20B). The bushings 292, 294 slideably engage the body portion 96 of the piston 92. The bushing(s) are formed for very close tolerance to the local dimension of the plunger to enable translational movement along the actuation axis 48 while restricting lateral motion between the housing 42 or 242 and the piston assembly 62 or 262. In one embodiment, the bushings 292, 294 are fabricated from PTFE.

Functionally, the bushings 292, 294 help maintain the piston assembly 62 or 262 in proper alignment with housing 42 or 242, despite the presence side forces that may be imposed on the control handle 38. The control handle 38, being of a plunger type design, can be axisymmetric about the actuation axis 48 and therefore has no inherently proper rotational orientation of operation. Accordingly, the operator may impose a force on the distal portion 66 of the plunger assembly 62 or 262 having a force component that is parallel to the rotation axis 109 of the gear 102. If unchecked, a force in this direction imposed at the distal portion 66 can cause the gear rack(s) 284, 284a or 284b to deflect laterally relative to the gear 102. Such lateral deflection can cause unwanted interference between the gear rack teeth 286, 286a or 286b and the gear teeth 104 during deflection of the steering section 32. The bushings 292, 294 can act to counter side forces applied to the control handle 38, thereby reducing lateral deflections.

For the switching operation, when the rotatable housing 242b is in the first rotational orientation, the switch pin 224 is aligned with the first guide slot 226a and is substantially centered on the first guide axis 238a (FIG. 20A). In this first rotational orientation 206, actuation of the plunger assembly 262 causes the switch pin 224 to slide along the first guide axis 238a. Also in this first rotational orientation 206, when the plunger assembly 262 has been actuated such that the switch pin 224 is not adjacent the lateral slot 234, the switch pin 224 is captured within the first guide slot 226a such that the rotatable housing portion 242b cannot be rotated, and the only relative motion between the housing 242 and the plunger assembly 262 is translation along the actuation axis 48. Functionally, the interaction between the switch pin 224 and the first guide slot 226a maintains tangential alignment between the gear 102 and the first gear rack 284a.

With the rotatable housing portion 242b in the first rotational orientation 206, actuation of the plunger assembly 262 along the actuation axis 48 causes the gear 102 and attendant spooling portion 112 to rotate in a first rotational direction 252 about the rotation axis 109. From the perspective of FIGS. 20A and 20B, movement of the plunger assembly 262 in the distal direction 54 relative to the housing 242 causes a clockwise rotation of the gear 102 about the rotation axis 109 (depicted), and actuation in the proximal translational direction 52 causes a counterclockwise rotation. This action gathers in and exerts a tension on the pull wire end portion 36a, while letting out pull wire end portion 36b. The tension exerted on the pull wire end portion 36a is transferred to the steering section 32, causing the distal portion 28 of the catheter assembly 22 to deflect in the first lateral direction 152.

When the rotatable housing 242b is in the second rotational orientation 208, the switch pin 224 is aligned with the second guide slot 226b and is substantially centered on the second guide axis 238b (FIG. 21A). In this second rotational orientation 208, actuation of the plunger assembly 262 causes the switch pin 224 to slide along the second guide axis 238b. Also in this second rotational orientation 208, when the plunger assembly 262 has been actuated such that the switch pin 224 is not adjacent the lateral slot 234, the switch pin 224 is captured within the second guide slot 226b such that the rotatable housing portion 242b cannot be rotated, and the only relative motion between the housing 242 and the plunger assembly 262 is translation along the actuation axis 48. Functionally, the interaction between the switch pin 224 and the second guide slot 226a maintains axial alignment between the gear 102 and the second gear rack. 284b.

With the rotatable housing portion 242b in the second rotational orientation 208, actuation of the plunger assembly 262 along the actuation axis 48 causes the gear 102 and attendant spooling portion 112 to rotate in a second rotational direction 254 about the rotation axis 109. From the perspective of FIGS. 21A and 21B, movement of the plunger assembly 262 in the distal direction 54 relative to the housing 242 causes a counterclockwise rotation of the gear 102 about the rotation axis 109 (depicted), and actuation in the proximal translational direction 52 causes a clockwise rotation. This action gathers in and exerts a tension on the pull wire end portion 36b, while letting out pull wire end portion 36a. The tension exerted on the pull wire end portion 36b is translated to the steering section 32, causing the distal portion 28 of the catheter assembly 22 to deflect in the second lateral direction 154.

Switching from the first rotational orientation 206 to the second rotational orientation 208 is accomplished with the switching mechanism 220 as follows: The plunger assembly 262 is fully retracted within the housing 242 so that the switch pin 224 registers against the distal end 232a of the first guide slot 226a and adjacent the lateral slot 234. The registration of the switch pin 224 against the distal end 232a (or 232b) can act to define the limit of the retracted position of the piston assembly 262. Likewise, the switch pin can engage the proximal end 228a (or 228b) to define the limit of the extended position of the of the piston assembly 262.

The rotatable housing portion 242b is then rotated about the actuation axis 48 relative to the stationary housing portion 242a and the plunger assembly 262 so that the switch pin 224 passes through lateral slot 234 an into the distal end 232b of the second guide slot 226b. In the depicted embodiment, the catheter assembly 22 is in the neutral position (i.e., no deflection being induced by the control handle 38b during the switchover.

For embodiments utilizing the axial biasing element 240 mounted adjacent the lateral slot 234 (FIG. 18A), as the switch pin 224 passes through the lateral slot 234, the switch pin 224 passes over and makes contact with the engagement element 244, causing the engagement element 244 to retract into the cavity 246. The engagement element 244 can provide a biasing force on the switch pin 224 after the switch pin 224 passes over the center of the engagement element 244, thus providing a positive registration of the switch pin 224 into the distal end 232h of the second guide slot 226b. The passage of the switch pin 224 over the engagement element 244 can also provide an audible sound that informs the operator that the switchover is complete.

For embodiments utilizing the radial biasing element(s) 280 (FIG. 19), the operation of each radial biasing element 280 is as follows: When the switch pin 224 is within the first guide slot 226a, the radial biasing element(s) is registered within the first axially extending groove 282a. As the rotatable housing portion 242b is rotated relative to the stationary housing portion 242a to cause the switch pin 224 to pass through the lateral slot 234, the engagement element 285 of the radial biasing element 280 passes over the exterior surface 98 of the body portion 96 of the plunger 92 that is between the axially extending grooves 282a and 282b, causing the engagement element 285 to retract. As the switch pin 224 becomes aligned with the second guide slot 226b, the radial biasing element 280 becomes aligned with the second axially extending groove 282b, causing the engagement element 285 of the radial biasing element 280 to engage with the second axially extending groove 282b. The engagement action can provide an audible sound that informs the switchover is complete.

To switch from the second rotational orientation 208 to the first rotational orientation 206, the sequence is reversed. That is, the plunger assembly 262 is fully retracted within the housing 242, registering switch pin 224 registers against the distal end 232b of the second guide slot 226b, and the rotatable housing portion 242b rotated so that the switch pin 224 passes through lateral slot 234 an into the distal end 232a of the first guide slot 226a. The various biasing arrangements operate in the same manner as described above, but in reverse.

Accordingly, for the depicted embodiments of FIGS. 10-21, the rotatable housing portion 242b can only be rotated when the switch pin 224 of the rotatable housing portion 242b is adjacent the lateral slot 234, i.e., is located at the distal end 232a or 232b of the respective guide slot 226a or 226b. In one embodiment, when the switch pin is located at the distal end 232a or 232b, the catheter assembly 22 is in the neutral position (i.e., no deflection being induced by the control handle 38b).

As discussed attendant to FIG. 13B, one embodiment of the control handle 38b is configured so that both the gear racks 248a and 248b engage the gear 102 during the switchover. Functionally, this helps prevent the catheter assembly 22 from changing shape during the switchover. While the so-called "neutral" position does not involve any deflection being induced by the control handle 38b, there are still generally forces acting on the catheter during a surgical procedure. The catheter assembly 22 can assume a very tortuous route to deliver the end effector 34 to the desired destination, causing several bends in the catheter assembly. The bending can cause strain on the pull wire(s) 36 that would act on the gear 102 if the gear 102 were released, causing the gear 102 to assume a different rotational orientation when in the "neutral" position. This could lead to a number of undesired complications, such as reduced articulation for the distal end 28 in one lateral direction, over articulation of the distal end 28 in the other lateral direction, and an imposed deflection on the distal end 28 when the handle 38a is in the so-called "neutral" position. By affirmatively capturing the gear 102 during the switchover, these complications are avoided.

The ability to switch the rotation of the gear 102 and attendant spool portion 112 provides the higher resolution in the control of the deflection of the distal portion 28 of the catheter assembly 22 because the deflections in the first and second lateral directions 152 and 154 do not have to be limited half the stroke length 130 of the handle 38*b*. The ability to reverse the rotational direction of the gear 102 relative to the direction of actuation negates the need to limit each direction of deflection to half the stroke length 130. That is, in the first rotational orientation, the gear 102 rotates in the first rotational direction 252 across the entire stroke of the piston assembly; in the second rotational orientation, the gear rotates in the opposite, second rotational direction 254 across the entire stroke of the piston assembly. Accordingly, the operator is afforded more resolution when deflecting the distal portion 28 of the catheter assembly 22.

All of the features disclosed in this specification (including any accompanying claims, abstract and drawings), and/or all of the steps of any method or process so disclosed, can be combined in any combination, except combinations where at least some of such features and/or steps are mutually exclusive.

Each feature disclosed in this specification (including any accompanying claims, abstract and drawings) can be replaced by alternative features serving the same, equivalent or similar purpose, unless expressly stated otherwise. Thus, unless expressly stated otherwise, each feature disclosed is one example only of a generic series of equivalent or similar features.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A medical device, comprising:
   a deflectable shaft;
   a handle coupled to the deflectable shaft, comprising:
   a deflection actuator movable along an actuation axis over an actuation area;
   a selectable switching mechanism having at least two switch deflection positions, each of the switch deflection positions corresponding to a different direction of deflection for which the deflectable shaft will deflect upon actuation of the deflection actuator;
   at least first and second mating surfaces within the handle, wherein the position of the first and second surfaces is dependent upon a selected one of the switch deflection positions; and
   a rotating member coupled to at least first and second steering wires in the deflectable shaft, the rotating member configured to engage the first mating surface when the switch deflection position is in a first position to retract the first pull wire around the rotating member when the deflection actuator is moved along the actuation axis over the actuation area, and further configured to engage the second mating surface when the switch deflection position is in a second position to retract the second pull wire around the rotating member when the deflection actuator is moved along the actuation axis along the same actuation area.

2. The medical device of claim 1, wherein the rotating member is configured to rotate in a first direction to retract the first pull wire around the rotating member when the switch deflection position is in the first position, and wherein the rotating member is configured to rotate in a second direction to retract the second pull wire around the rotating member when the switch deflection position is in the second position.

3. The medical device of claim 1, wherein the deflection actuator is movable over a full stroke length of the actuation area when the switch deflection position is in the first position to retract the first pull wire around the rotating member, and wherein the deflection actuator is movable over the same full stroke length of the actuation area when the switch deflection position is in the second position to retract the second pull wire around the rotating member.

4. The medical device of claim 1, wherein the deflection actuator is movable along the actuation axis substantially parallel to a longitudinal axis of the handle.

5. The medical device of claim 4, wherein the deflection actuator comprises a plunger mechanism movable along the actuation axis substantially parallel to a longitudinal axis of the handle.

6. The medical device of claim 1, wherein the rotating member comprises a rotating gear, and wherein the first and second mating surfaces respectively comprise first and second mating gear teeth.

7. The medical device of claim 6, wherein the rotating gear is coupled to the first and second steering wires in the deflectable shaft, the rotating gear is configured to engage the first gear teeth when the switch deflection position is in the first position to retract the first pull wire around the rotating gear when the deflection actuator is moved along the actuation axis over the actuation area, and is further configured to engage the second gear teeth when the switch deflection position is in the second position to retract the second pull wire around the rotating gear when the deflection actuator is moved along the actuation axis along the same actuation area.

8. The medical device of claim 6, wherein the first and second gear teeth are asymmetrically positioned in the handle such that the rotating gear engages only one of the first and second gear teeth at a time, depending on the switch deflection position that is selected.

9. The medical device of claim 1, wherein the selectable switching mechanism comprises a knob rotatable about the actuation axis.

10. The medical device of claim 1, further comprising a first anchor point on the rotating member to which the first pull wire is attached, and comprising a second anchor point on the rotating member to which the second pull wire is attached.

11. A medical device, comprising:
    a deflectable shaft;
    a handle coupled to the deflectable shaft, comprising:
    a plunger moveable within the handle over an actuation area;
    a switching mechanism to selectively change a direction of deflection between a first deflection direction and a second deflection direction of the deflectable shaft;
    means for deflecting the deflectable shaft in the first deflection direction in response to the plunger being moved over the actuation area when the switching mechanism is in a first position; and
    means for deflecting the deflectable shaft in the second deflection direction in response to the plunger being moved over the same actuation area when the switching mechanism is in a second position.

12. The medical device of claim 11, wherein the means for deflecting the deflectable shaft in the first deflection direction comprises means for retracting a first pull wire to deflect the deflectable shaft in the first deflection direction in response to moving the plunger distally when the switching mechanism is in the first position, and wherein the means for deflecting the deflectable shaft in the second deflection direction comprises means for retracting a second pull wire to deflect the deflectable shaft in the second deflection direction in response to moving the plunger distally within the same actuation area when the switching mechanism is in the second position.

13. The medical device of claim 12, wherein the plunger is movable over a full stroke length of the actuation area when the switching mechanism is in the first position to retract the first pull wire, and wherein the plunger is movable over the same full stroke length of the actuation area when the switching mechanism is in the second position to retract the second pull wire.

14. The medical device of claim 11, wherein the switching mechanism comprises a knob rotatable about the actuation axis.

15. A method for deflecting a catheter shaft from an attached catheter handle, comprising:
   facilitating movement of a plunger relative to the catheter handle over an actuation area;
   facilitating user selection of a first deflection direction or a second deflection direction;
   deflecting the catheter shaft in a first direction by facilitating movement of the plunger over the actuation area when the first deflection direction is selected; and
   deflecting the catheter shaft in a second direction by facilitating movement of the plunger over the actuation area when the second deflection direction is selected.

16. A method for deflecting a catheter shaft from an attached catheter handle, comprising:
   facilitating movement of a plunger in a first plunger direction relative to the catheter handle;
   facilitating user selection of a first deflection direction or a second deflection direction via a switching mechanism;
   deflecting the catheter shaft in a first direction when the first deflection direction is selected and the plunger is moved in the first plunger direction; and
   deflecting the catheter shaft in a second direction when the second deflection direction is selected and the plunger is moved in the first plunger direction.

* * * * *